United States Patent
Bar-Zohar et al.

(10) Patent No.: US 7,480,402 B2
(45) Date of Patent: Jan. 20, 2009

(54) SYSTEM AND METHOD FOR PRODUCING AN AUGMENTED IMAGE OF AN ORGAN OF A PATIENT

(75) Inventors: Meir Bar-Zohar, Haifa (IL); Avi Yaron, Tenafly, NJ (US)

(73) Assignee: Visionsense Ltd., Petah Tikva (IL)

( * ) Notice: Subject to any disclaimer, the term of this patent is extended or adjusted under 35 U.S.C. 154(b) by 0 days.

(21) Appl. No.: 11/912,099

(22) PCT Filed: Apr. 20, 2006

(86) PCT No.: PCT/IL2006/000474

§ 371 (c)(1),
(2), (4) Date: Oct. 19, 2007

(87) PCT Pub. No.: WO2006/111965

PCT Pub. Date: Oct. 26, 2006

(65) Prior Publication Data

US 2008/0144773 A1    Jun. 19, 2008

Related U.S. Application Data

(60) Provisional application No. 60/673,257, filed on Apr. 20, 2005.

(51) Int. Cl.
G06K 9/00 (2006.01)
(52) U.S. Cl. .................. 382/131; 382/128; 382/154
(58) Field of Classification Search .......... 382/128, 382/131, 132, 133, 154; 250/461.2, 389; 356/435; 347/251, 253; 346/135.1; 378/98.2, 378/19, 4, 98.12; 348/E13.005; 600/508, 600/509, 437
See application file for complete search history.

(56) References Cited

U.S. PATENT DOCUMENTS

| 5,400,147 | A | * | 3/1995 | Korn et al. | 347/253 |
| 5,448,610 | A | * | 9/1995 | Yamamoto et al. | 378/19 |
| 5,805,663 | A | * | 9/1998 | Mihara | 378/98.2 |
| 5,961,454 | A |   | 10/1999 | Kooy et al. | 530/387.7 |

(Continued)

OTHER PUBLICATIONS

Dey et al., "Automatic Fusion of Freehand Endoscopic Brain Images to Three-Dimensional Surfaces: Creating Stereoscopic Panoramas", IEEE, vol. 21, No. 1, Jan. 2002, pp. 23-30.*

(Continued)

*Primary Examiner*—Anh Hong Do
(74) *Attorney, Agent, or Firm*—Merchant & Gould P.C.

(57) ABSTRACT

System for displaying an augmented image of an organ of a patient, including an image fusion processor coupled with a stereoscopic image detector, a tomographic image processor, and with a display, the tomographic image processor being further coupled with a tomographic image detector, the stereoscopic image detector producing a pair of stereoscopic images respective of an exposed region of the organ, the tomographic image detector acquiring at least one two dimensional image of a concealed region of the organ, the concealed region being concealed from the view of the stereoscopic image detector, the tomographic image processor producing at least one tomographic image representation of the concealed region, according to an output of the tomographic image detector, the image fusion processor registering the pair of stereoscopic images with the tomographic image representation, the image fusion processor producing the augmented image, by superimposing the tomographic image representation on the pair of stereoscopic images, the display displaying the augmented image.

37 Claims, 6 Drawing Sheets

U.S. PATENT DOCUMENTS

| | | | |
|---|---|---|---|
| 6,078,681 A * | 6/2000 | Silver | 382/133 |
| 6,319,201 B1 | 11/2001 | Wilk | 600/437 |
| 6,815,687 B1 * | 11/2004 | Branch-Sullivan et al. | 250/389 |
| 6,990,231 B2 * | 1/2006 | Goto | 382/154 |
| 7,144,376 B2 * | 12/2006 | Nakai et al. | 600/508 |

OTHER PUBLICATIONS

Spetsieris et al., "Visuo-Computational Tools for PET Physiological Imaging", IEEE, vol. 3, Nov. 1991, pp. 2149-2153.*

* cited by examiner

SYSTEM AND METHOD FOR PRODUCING AN AUGMENTED IMAGE OF AN ORGAN OF A PATIENT

FIELD OF THE DISCLOSED TECHNIQUE

The disclosed technique relates to augmented reality systems in general, and to methods and systems for producing an augmented image of an organ of a patient, in particular.

BACKGROUND OF THE DISCLOSED TECHNIQUE

Minimally invasive surgeries (MIS) are quite common these days. Not until very long ago, surgeries on the organs of a patient were performed by dissecting a substantially large portion of the body in the vicinity of the organ, in order to gain access to an organ. These surgeries involved many health complications after the surgery, thereby elongating the hospital stays, and raising the cost of the surgery. But nowadays, with the advent of computerized medical devices, it is possible to perform a topical incision (hence the term MIS), to gain access to the specific region of the organ, thereby allowing a greater portion of the society to gain access to the health services.

For example, in the past, the surgeon had to cut open the region of the abdomen above the liver, in order to be able to remove a tumor within the liver. But now, the surgeon identifies the exact location of the tumor in a computer tomography (CT) image prior to the surgery, and penetrates two small diameter medical devices through the abdomen, one for incision of the tissue of the liver and another for performing a suture after removal of the tumor, according to the identified location. In order to perform the surgery with these two devices, the surgeon penetrates also a medical vision device (i.e., an endoscope) close to these two devices, in order to obtain a real-time video image of the region of the surgery. This real-time video image can be displayed on a display, alongside the CT image of the liver, which was acquired preoperatively.

Reference is now made to FIG. 1, which is a schematic illustration of a system generally referenced 50, for performing a minimally invasive operation on an organ of a patient, as known in the art. System 50 includes a computer tomography (CT) image detector 52, a processor 54, an integral videography (IV) display 56, a surgical instrument 58, and an optical tracking system 60. IV display 56 includes a liquid crystal display (LCD) 62 with a microconvex lens array, and a half-silvered mirror 64. CT image detector 52 is associated with processor 54. Each of surgical instrument 58 and IV display 56 includes a plurality of optical probes (not shown). Optical tracking system 60 is connected with processor 54, and with the optical probes of surgical instrument 58 and of IV display 56.

Prior to the surgery, CT image detector 52 acquires a set of image slices 68 of a brain 66 of a patient 70, and stores the set of image slices 68 in processor 54. During the surgery, a skull 72 of patient 70 is fixed under half-silvered mirror 64, while a surgeon (not shown) penetrates surgical instrument 58 into skull 72. Processor 54 produces a CT image 74 of brain 66, according to the set of image slices 68, and projects CT image 74 on LCD 62. Eyes 76 of the surgeon detect an image of skull 72 through a light beam 78 which passes through half-silvered mirror 64, and also an auto-stereoscopic view of CT image 74 through a light beam 80, which is reflected from half-silvered mirror 64.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
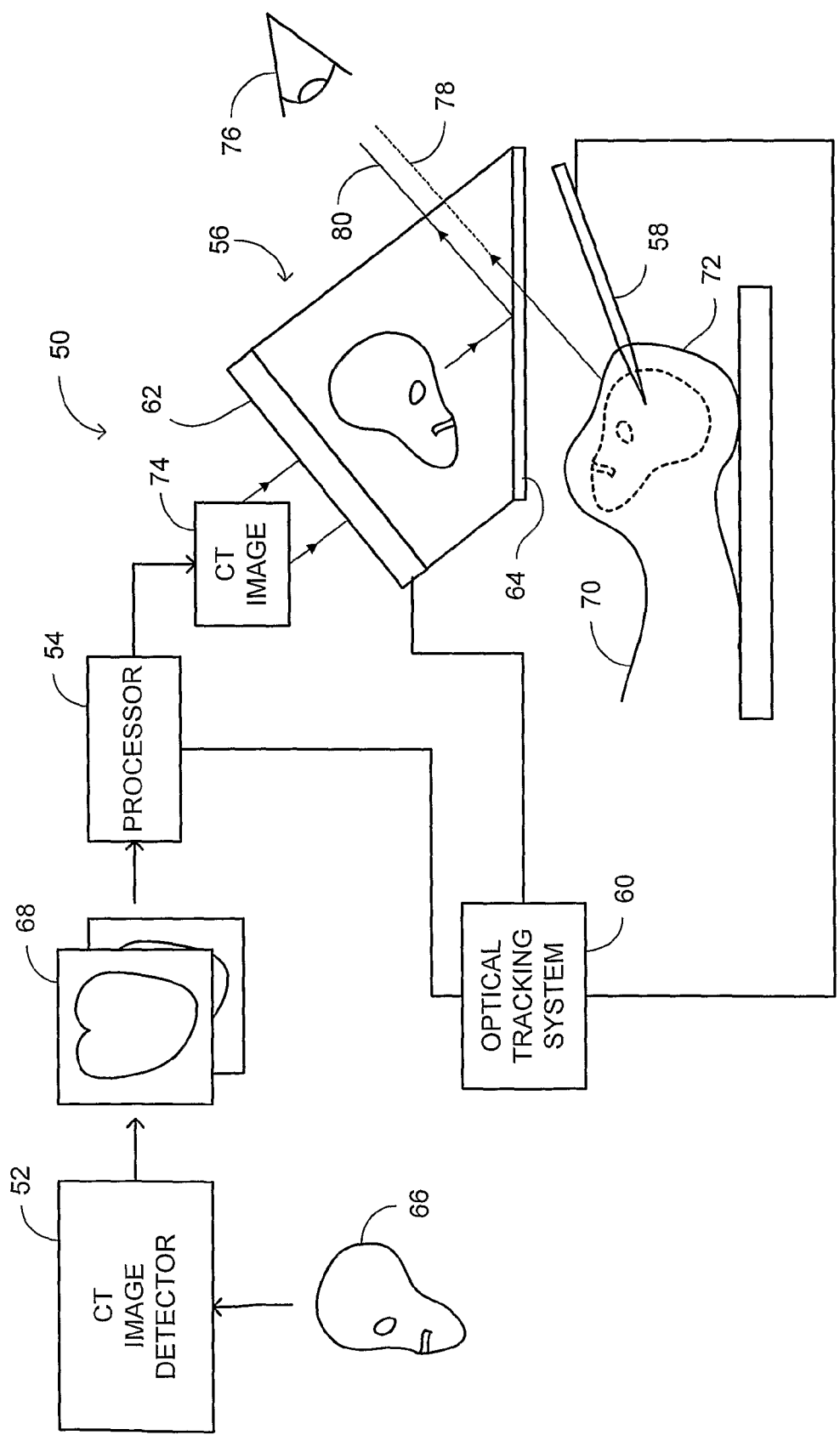
FIG. 1 is a schematic illustration of a system for performing a minimally invasive operation on an organ of a patient, as known in the art.

The disclosed technique overcomes the disadvantages of the prior art by fusing a stereoscopic image pair of an organ of a patient, with a tomographic image representation of the organ. The fused image which is displayed on a display, includes the tomographic image representation superimposed on the stereoscopic image pair, while providing a stereoscopic perception of the fused image to a user. The stereoscopic image pair can be acquired by an endoscope which is penetrated into the body of the patient (e.g., during a laparoscopy operation on the liver). The tomographic image representation can be either a single two-dimensional (2D) image, detected by a tomographic image detector, a three-dimensional (3D) image reconstructed from a plurality of 2D images detected by the tomographic image detector, or a stereoscopic image reconstructed according to the tomographic image representation.

The tomographic image representation can be acquired either during the medical operation (real-time), for example, by an ultrasound image detector, infrared image detector, and the like, or prior to the medical operation (preoperative), for example by computer tomography (CT), magnetic resonance imager (MRI), positron emission tomography (PET), single photon emission computer tomography (SPECT), and the like. A segmentation algorithm can be applied to the 2D image as well as to the 3D reconstructed image, in order to highlight a selected feature of the organ (e.g., a tumor, blood vessels), thereby enabling the user to view a superposition of the tumor against the stereoscopic image pair.

The term "tomographic image detector" herein below, refers to an image detector which can acquire a plurality of 2D images from concealed regions of an organ of a patient, which a visible light image detector is incapable to detect. The tomographic image detector can be a CT, MRI, PET, SPECT, ultrasound image detector, infrared image detector, X-ray imager, and the like. The tomographic image detector, can produce a 3D reconstructed image of the organ, according to the 2D images detected thereby, from the concealed regions of the organ. This 3D reconstructed image provides the user, visible information respective of a volume of the organ. The tomographic image detector can acquire an image of the organ either prior to the medical operation (i.e., preoperative image detector), such as CT, MRI, PET, SPECT, or in real-time (i.e., real-time image detector), as in the case of ultrasound, infrared, and X-ray.

The term "endoscope" herein below refers to a medical device which can be penetrated in the body of a patient during a minimally invasive surgery (e.g., laparoscopy), in order to acquire real-time video images of the organ from two different view points, thereby providing a stereoscopic perception when the video image is viewed by the user on a display. The endoscope can be employed for performing diagnosis or operation on different organs, such as colon, kidneys, liver, lungs, heart, esophagus, larynx, trachea, urethra, ureter, brain, bladder, and the like. The endoscope includes a stereoscopic image detector, to acquire a right view image and a left view image of an exposed region of the organ (e.g., the envelope of the liver before an incision, or optically visible inner regions of the liver after the incision). The stereoscopic image detector can include either a single image detector (as described herein below in connection with FIG. 5), or two image detectors to detect the right view image and the left view image.

The term "stereoscopic image pair" herein below, refers to a pair of images acquired by the stereoscopic image detector, which when processed by an image processor and displayed on a display, provides a stereoscopic perception to the user. Therefore, the term "stereoscopic image pair" refers to a pair of right and left view images of an object. The term "tomographic image representation" herein below, refers to a representation of an image of the organ acquired by the tomographic image detector, which the image processor fuses with the stereoscopic image pair, to be displayed together on the display. As described herein above, the tomographic image representation can be either a 2D image, a 3D reconstructed image, or a reconstructed stereoscopic image. Alternatively, the tomographic image representation can represent a selected feature associated with the organ (e.g., a tumor, organ vasculature, organ nerves).

Figure 2:
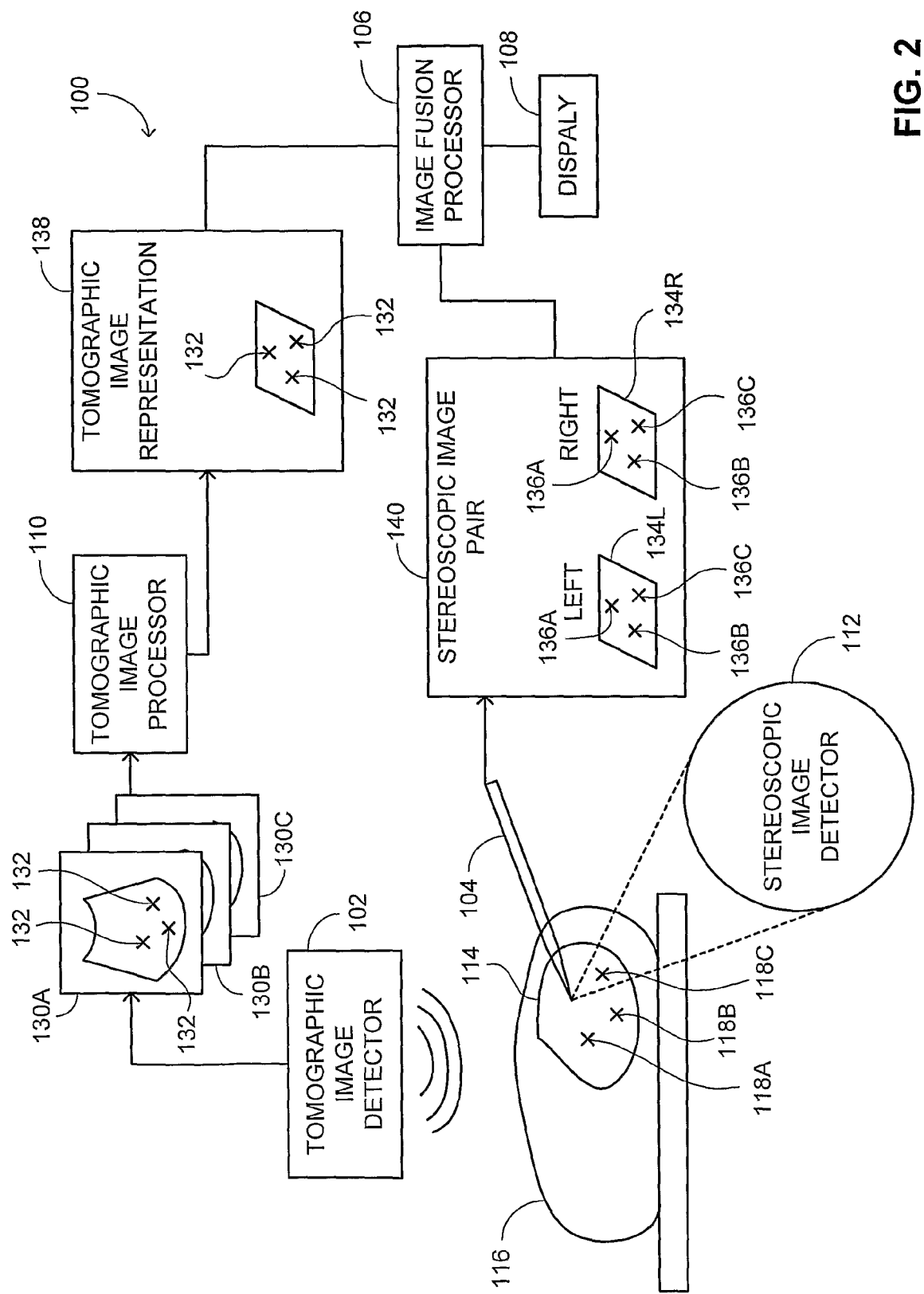
FIG. 2 is a schematic illustration of a system for providing a stereoscopic visualization of a tomographic image representation of an organ, fused with a video image of the external surface of the organ, constructed and operative in accordance with an embodiment of the disclosed technique.
Figure 3A:
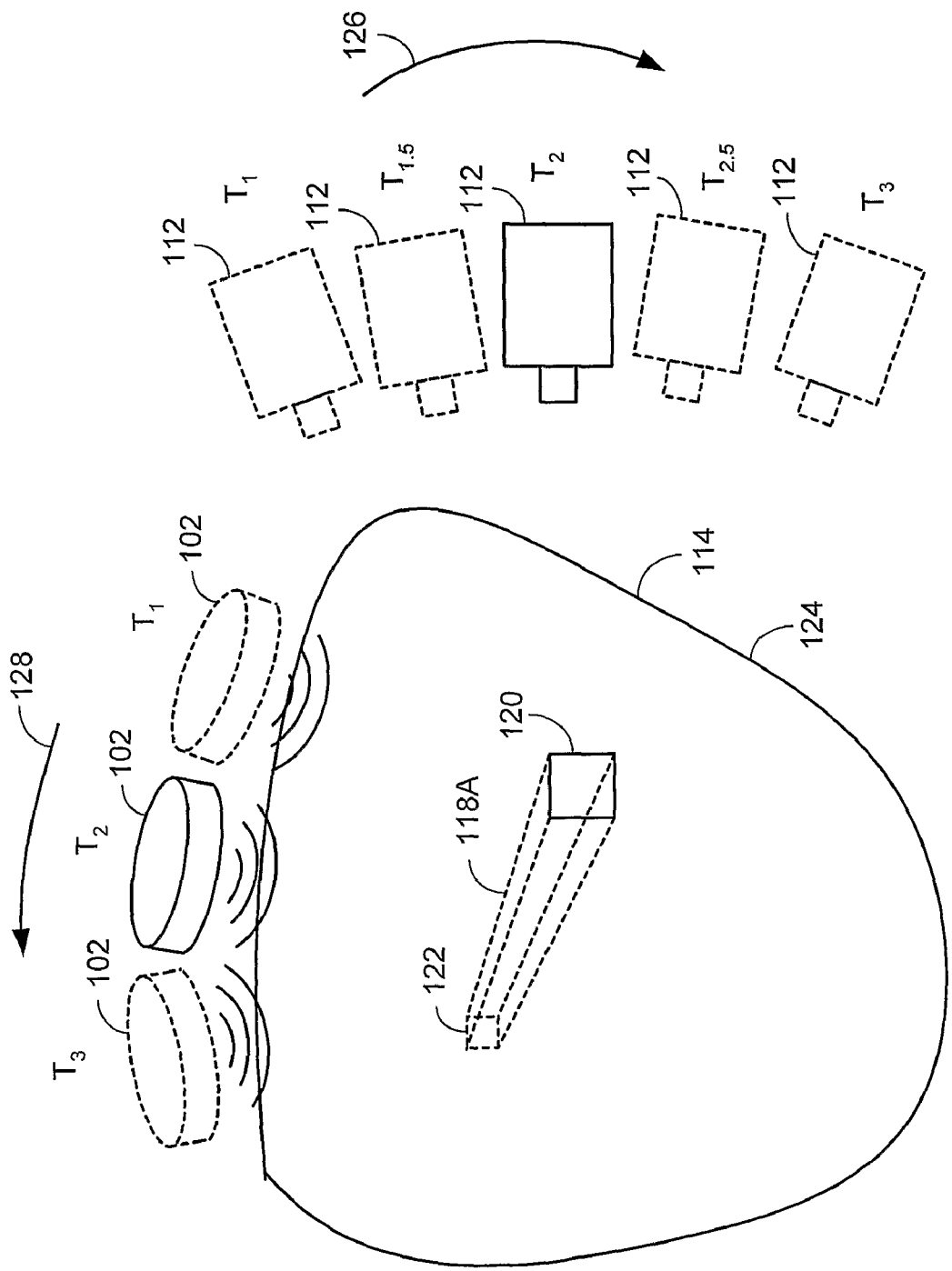
FIG. 3A is a schematic illustration of the organ of FIG. 2, being simultaneously detected by the tomographic image detector of FIG. 2 and the stereoscopic image detector of FIG. 2, wherein a fiducial is penetrated in the organ.
Figure 3B:
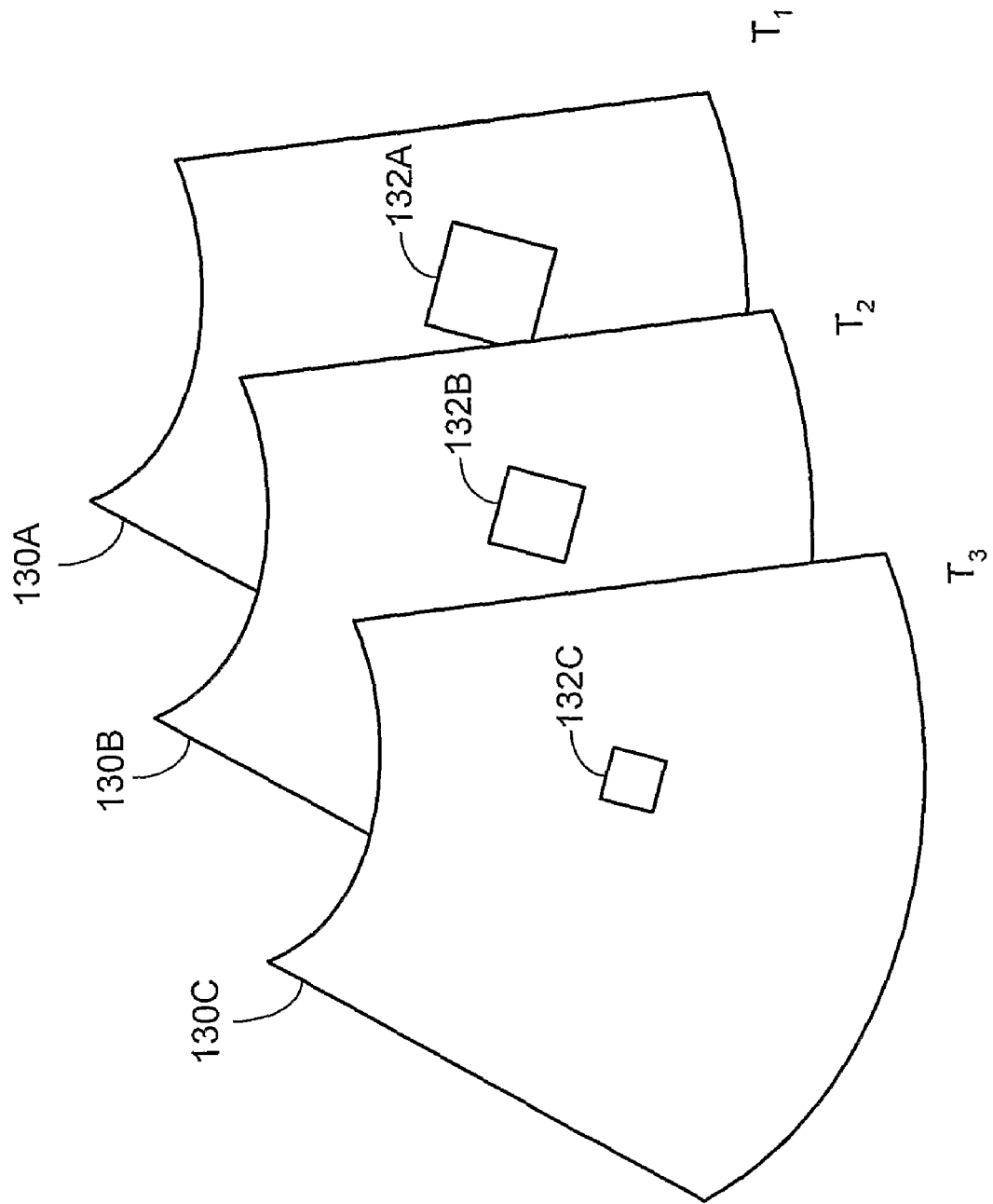
FIG. 3B is a schematic illustration of images of the cross section of the fiducial of FIG. 3A, in different 2D images of the organ being detected by the tomographic image detector of FIG. 2.
Figure 4:
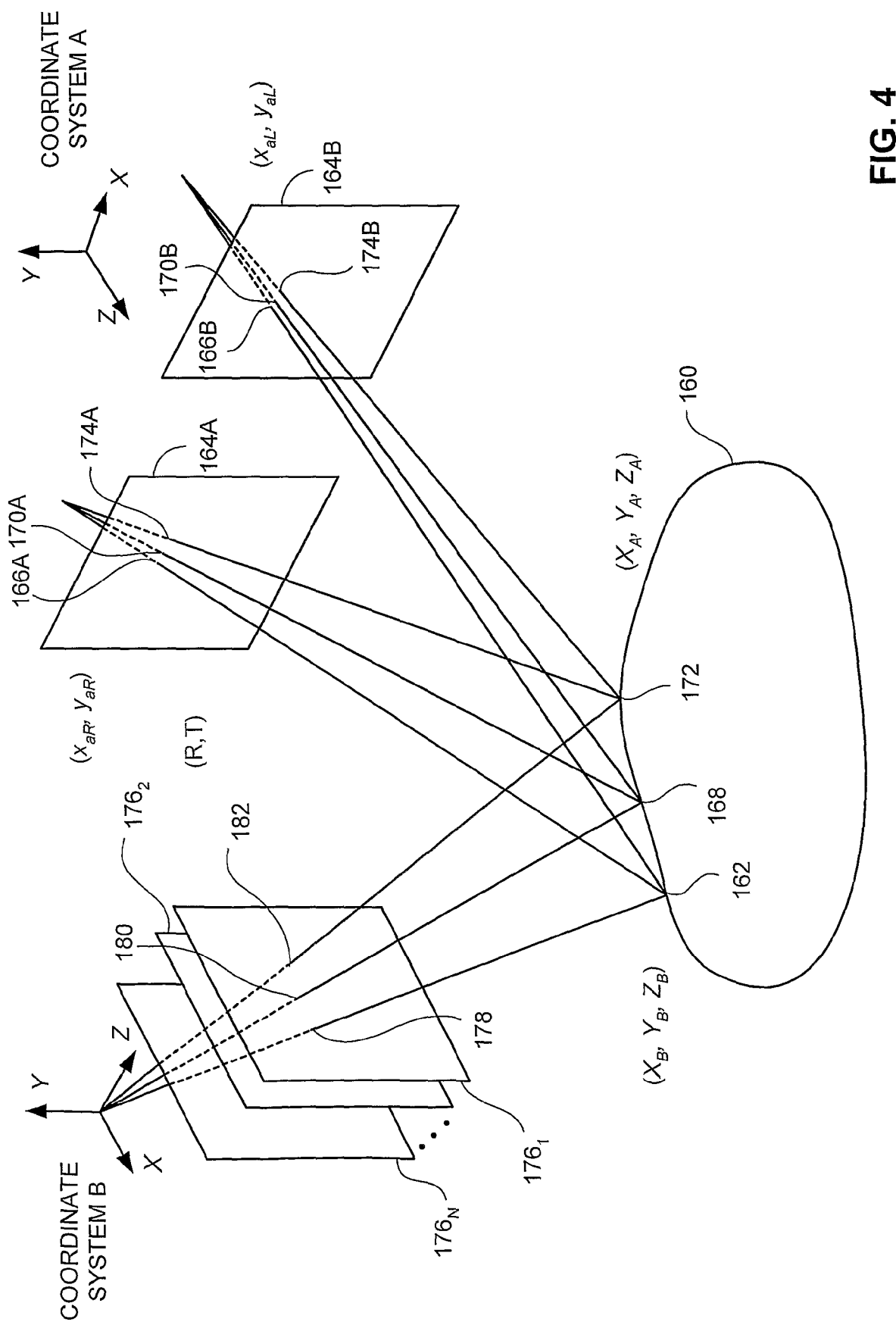
FIG. 4 is a schematic illustration of three points on an object, being projected on a right image plane and a left image plane of the stereoscopic image detector of FIG. 2, and on a plurality of tomographic image planes of the tomographic image detector of FIG. 2.

Reference is now made to FIGS. 2, 3A, 3B and 4. FIG. 2 is a schematic illustration of a system generally referenced 100, for providing a stereoscopic visualization of a tomographic image representation of an organ, fused with a video image of the external surface of the organ, constructed and operative in accordance with an embodiment of the disclosed technique. FIG. 3A is a schematic illustration of the organ of FIG. 2, being simultaneously detected by the tomographic image detector of FIG. 2, and the stereoscopic image detector of FIG. 2, wherein a fiducial is penetrated in the organ. FIG. 3B is a schematic illustration of images of the cross section of the fiducial of FIG. 3A, in different 2D images of the organ being detected by the tomographic image detector of FIG. 2. FIG. 4 is a schematic illustration of three points on an object, being projected on a right image plane and a left image plane of the stereoscopic image detector of FIG. 2, and on a plurality of tomographic image planes of the tomographic image detector of FIG. 2.

System 100 includes a tomographic image detector 102, an endoscope 104, an image fusion processor 106 and a display 108. Tomographic image detector 102 is associated with a tomographic image processor 110. Endoscope 104 includes a stereoscopic image detector 112. Image fusion processor 106 is coupled with tomographic image processor 110, stereoscopic image detector 112 and with display 108.

Display 108 can be a cathode ray tube (CRT) display, autostereoscopic display, head-mounted display, volumetric display, multi-LCD (liquid crystal display) display, and the like. The CRT display displays a right view image and a left view image of an object polarized at different polarization states. A user wearing a suitable pair of polarized glasses, can gain a stereoscopic perception when viewing the display. The volumetric display includes a rapidly spinning round plastic projection screen which bounces off light beams projected from below, toward the user.

The multi-LCD display includes an array of LCD's arranged in parallel. Only one LCD at a time produces an image, while the rest are set to a transparent state. By setting each LCD to produce an image in sequence, the multi-LCD display produces a perception of depth. Both the volumetric display and the multi-LCD display, display a volumetric image where the brain does not have to process a right view image and a left view image to gain a stereoscopic perception of an image. However, the CRT display of a right view image and a left view image is a more natural experience, because this is the way the human brain is adapted to process visual images of objects detected by the eyes. In the following description, tomographic image detector 102 is a real-time image detector (e.g., ultrasound image detector), and the medical operation involves a liver 114 of a patient 116.

Endoscope 104 is penetrated in the abdomen (not shown) of patient 116, in order to acquire video images of a selected portion 124 (FIG. 3A) of liver 114, during the medical operation. Endoscope 104 moves on an endoscope plane (not shown), for example in a direction referenced by an arrow 126. Tomographic image detector 102, in this case an ultrasound transducer, moves on an scanning plane (not shown) different than the endoscope plane, for example in a direction referenced by an arrow 128, in order to acquire a plurality of 2D images 130A (FIG. 3B), 130B, and 130C (i.e., a tomographic image representation 138).

Stereoscopic image detector 112 acquires a right view image 134R and a left view image 134L (i.e., a stereoscopic image pair 140) of a selected portion 124 of liver 114. Tomographic image detector 102 acquires images 130A, 130B, and 130C at a rate $R_{TOMOGRAPHY}$, at times $T_1$, $T_2$, and $T_3$, respectively. Stereoscopic image detector 112 acquires a plurality of stereoscopic image pairs similar to stereoscopic image pair 140, at a rate $R_{ENDOSCOPE}$, at times $T_1$, $T_{1.5}$, $T_2$, $T_{2.5}$, and $T_3$. $R_{TOMOGRAPHY}$ can be either smaller, substantially equal to, or greater than $R_{ENDOSCOPE}$. Image fusion processor 106 receives images 130A, 130B, and 130C from tomographic image detector 102, and the stereoscopic image pairs from stereoscopic image detector 112.

Tomographic image representation 138 can be a single 2D tomographic image, for example, one acquired by an ultrasound image detector of a CT. Alternatively, tomographic image representation 138 can be a 3D image, reconstructed for example, according to a plurality of 2D tomographic images acquired by a CT. Further alternatively, tomographic image representation 138 can be a stereoscopic image (i.e., computed stereoscopic image), reconstructed according to tomographic image representation 138.

Image fusion processor 106 registers tomographic image representation 138 with stereoscopic image pair 140, according to a method known the art. Image fusion processor 106 registers tomographic image representation 138 with stereoscopic image pair 140, by determining a transformation matrix between tomographic image representation 138 and stereoscopic image pair 140. Image fusion processor 106 applies this transformation matrix on every pixel of either one of tomographic image representation 138 or stereoscopic image pair 140, in order to register tomographic image representation 138 with stereoscopic image pair 140.

Image fusion processor 106 superimposes tomographic image representation 138 on stereoscopic image pair 140, thereby producing an augmented stereoscopic image (not shown) of selected portion 124. It is noted that image fusion processor 106 performs the image registration and the superposition procedures in real-time, on every frame detected by each of stereoscopic image detector 112 and tomographic image detector 102. It is further noted that prior to the process of registration, image fusion processor 106 can perform a segmentation algorithm known in the art, to tomographic image representation 138, for example to highlight a tumor in the organ.

Image fusion processor 106 can register tomographic image representation 138 with stereoscopic image pair 140, by employing a position and orientation determining system (not shown), known in the art (e.g., electromagnetic, optic, sonic). Alternatively, image fusion processor 106 can register tomographic image representation 138 with stereoscopic image pair 140, according to a landmark (not shown) respective of the organ. This landmark needs to be of such nature, that it can be detectable by both tomographic image detector 102 and stereoscopic image detector 112. This landmark can be an anatomic landmark (e.g., different features on the head of patient 116, such as nose and eyes) associated with the organ. Stereoscopic image detector 112 can detect this landmark, and tomographic image detector 102 can detect this landmark as well, in an external tomographic slice of the organ.

In case the organ is devoid of an anatomic landmark which can be detected by stereoscopic image detector 112 and tomographic image detector 102 (i.e., an organ having a smooth surface, e.g., liver 114), system 100 needs to employ at least one physical artificial landmark, such as fiduacials 118A (FIG. 2), 118B, and 118C, in the form of an elongated body, which are penetrated into the organ. Alternatively, fiducials 118A, 118B, and 118C can be attached to the surface of the organ. In either case (i.e., an anatomic landmark or a physical artificial landmark), image fusion processor 106 needs to identify at least three points respective of the landmark, in each of tomographic image representation 138 and stereoscopic image pair 140, and determine the 3D coordinates of each of these points, in order to determine the transformation matrix.

Tomographic image processor 110 provides image fusion processor 106, the 3D coordinates of the points respective of the landmark, in tomographic image representation 138, in a coordinate system respective of tomographic image detector 102. Image fusion processor 106 determines the X, and Y coordinates of each of the points respective of the landmark, in stereoscopic image pair 140, according to the index of the respective pixel in stereoscopic image pair 140. Image fusion processor 106 determines the Z coordinate (i.e., in a direction along an optical axis of stereoscopic image detector 112) of each of the points respective of the landmark, in stereoscopic image pair 140, according to the disparity value respective of the respective pixel, in stereoscopic image pair 140.

Each of fiducials 118A, 118B, and 118C is of such a property that enables image fusion processor 106 to determine the Z coordinate of an image of a certain slice of liver 114 (i.e., the distance of this slice from the surface of liver 114), detected by tomographic image detector 102. For this purpose, the fiducial can be for example, in the form of a conical pyramid. Image fusion processor 106 can determine the Z coordinate, by comparing the geometry of an image of a cross section of the fiducial in the current image, with the 3D geometry of the fiducial which is stored in a memory (not shown). Alternatively, the fiducial can be constructed from a plurality of layers, each having a different physical characteristic (e.g., responding differently to sound waves, in terms of amplitude or harmonics). In this case, image fusion processor 106 can identify the current layer and determine the Z coordinate of the current slice, by comparing the physical characteristic of the sound waves returned by the fiducial, with the one stored in the memory. This is the case where the direction of the ultrasound wave is not perpendicular to the longitudinal axis of the fiducial.

With reference to FIG. 3A, each of fiducials 118A, 118B, and 118C is in the form of a conical pyramid having a base 120 and a vertex 122. Base 120 protrudes from a local surface (not shown) of liver 114, while vertex 122 is located within liver 114. Alternatively, base 120 is substantially flush with the local surface of liver 114. Each of base 120 and vertex 122 can be in the form of a polygon, such as square, rectangle, triangle, pentagon, hexagon, parallelogram, trapezoid, and the like. Base 120 and vertex 122 are of substantially the same geometry, and the surface area of base 120 is greater than that of vertex 122. The geometrical data of each of fiducials 118A, 118B, and 118C is stored in the memory.

In case the cross section of a fiducial is in form of a polygon, system 100 is operative with a single fiducial. A fiducial of such form, can be constructed from a plurality of layers, having different physical characteristics, as described herein above. In case the cross section of the fiducial is in a form other than a polygon (e.g., circle, ellipse), and substantially uniform along the longitudinal axis thereof (e.g., in the form of a right circular cylinder), and the fiducial is constructed of a plurality of layers each having a different physical property, system 100 is operative with at least three of these fiducials.

Since the profile of fiducial 118A narrows down from base 120 to vertex 122, image 132B is smaller than image 132A, and image 132C is smaller than image 132B. Image fusion processor 106 determines the depth of image 130B relative to base 120, according to the geometry of image 132B relative to the respective geometry of base 120.

In case display 108 is a volumetric display, display 108 displays one of the right view 2D projection or the left view 2D projection. In this case, the user can not gain a stereoscopic perception of the augmented image displayed on display 108, however, he can perceive a volumetric perception of that augmented image. Alternatively, image fusion processor 106 can produce an interpolated superimposed image by interpolating between the right view 2D projection and the left view 2D projection, and display 108 can display the interpolated image.

Image fusion processor 106 can superimpose a set of right tomographic image representations on right view image 134R, and another set of left tomographic image representations on left view image 134L, during a selected time interval, thereby producing a right superimposed image and a left superimposed image. Image fusion processor 106 applies an attenuation function in the time domain, to the tomographic image representations in each set of the right tomographic image representations and the left tomographic image representations, such that the light intensity of the most recent tomographic image representations is the greatest, and that of the least recent tomographic image representations, is the least. Hence, the least recent tomographic image representations are less dominant and less apparent to the user, and thus the user is aware that the low intensity tomographic image representations belong to some time in the past, and will not detect the least recent tomographic image representations which are less accurate.

According to above example, where tomographic image detector 102 is an ultrasound image detector, tomographic image processor 110 produces tomographic image representation 138 in a polar coordinate system, whereas stereoscopic image detector 112 produces stereoscopic image pair 140, in a Cartesian coordinate system. In this case, image fusion processor 106 converts tomographic image representation 138 to the Cartesian coordinate system, while leaving stereoscopic image pair 140 in the Cartesian coordinate system, thereby producing an augmented image of selected portion 124 in the Cartesian coordinate system. Alternatively, image fusion processor 106 can convert stereoscopic image pair 140 to the polar coordinate system, while leaving tomographic image representation 138 in the polar coordinate system, thereby producing an augmented image of selected portion 124 in the polar coordinate system.

Further alternatively, the image fusion processor can determine the 3D coordinates according to both the stereoscopic image pair and the output of the position and orientation detectors (not shown), thereby providing a more accurate value of the depth, compared with each one alone, and enabling a more accurate registration of the stereoscopic image pair with the tomographic image representation.

Tomographic image representation 138 can be any of images 130A, 130B, and 130C. Alternatively, tomographic image representation 138 can be a segmented 2D image of a selected feature (e.g., a tumor, vasculature, nerves) of the organ (e.g., liver 114), which tomographic image processor 110 produces according to a segmentation technique known in the art. The end result of the fusion procedure performed by image fusion processor 106, is the segmented 2D image of selected portion 124 of liver 114, superimposed on a stereoscopic video visualization of the selected portion of liver 114, at substantially the same depth below the surface of liver 114. The segmented 2D image of the selected feature of liver 114 can be highlighted for example, by color, brightness, topography, and the like. Generally, tomographic image processor 110 performs image segmentation prior to the medical operation on patient 116.

Alternatively, tomographic image representation 138 can be a 3D reconstructed image of liver 114 which tomographic image processor 110 reconstructs according to images 130A, 130B, and 130C, by employing a technique known in the art. Image fusion processor 106, then fuses this 3D reconstructed image with stereoscopic image pair 140, as described herein below. Tomographic image processor 110 can reconstruct a segmented 3D reconstructed image of the selected feature of liver 114 (e.g., a tumor), according to a segmentation technique known in the art.

System 100 can further include a user interface (not shown) coupled with image fusion processor 106. The user can control one or more visual features (e.g., luminance, brightness, color, opacity) of each of the stereoscopic image pair and the tomographic image representation. In this manner, the user can for example, switch between appearance, disappearance of either of the stereoscopic image pair and the tomographic image representation, and modes in between, as displayed on the display. Additionally, image fusion processor 106 can correct the distortion in each of stereoscopic image pair 140 and tomographic image representation 138, according to an image distortion correction technique known in the art.

A tomographic image representation which is acquired by an infrared image detector, and fused with the stereoscopic image pair, can provide supplementary diagnostic information in addition to that provided by the stereoscopic image pair. For example, in case of a tumor under the surface of the organ, the stereoscopic image pair indicates a bulge related to the tumor, and the tomographic image representation includes additional information relating to a superficial region of the organ, thereby assisting the user to induce the fact that a tumor indeed exists.

Following is a description of the procedure for registering a 2D tomographic image detected by tomographic image detector 102, with stereoscopic image pair 140 (i.e., producing a registered tomographic image representation), where stereoscopic image pair 140 is regarded as a pair of 2D images (i.e., right view image 134R and left view image 134L). With further reference to FIG. 4, a three-dimensional object 160 (e.g., liver 114) is detected by tomographic image detector 102, and by stereoscopic image detector 112. Object 160 is associated with a first 3D coordinate system A (e.g., respective of stereoscopic image detector 112) and with a second 3D coordinate system B (e.g., respective of tomographic image detector 102). The optical center of stereoscopic image detector 112 is located at the origin of coordinate system A. The optical center of tomographic image detector 102 is located at the origin of coordinate system B.

The projections of a point 162 on the surface of object 160, on a right stereoscopic image plane 164A, and on a left stereoscopic image plane 164B of stereoscopic image detector 112, are referenced 166A and 166B, respectively. The projections of a point 168 on the surface of object 160, on right stereoscopic image plane 164A, and on left stereoscopic image plane 164B, are referenced 170A and 170B, respectively. The projections of a point 172 on the surface of object 160, on right stereoscopic image plane 164A, and on left stereoscopic image plane 164B, are referenced 174A and 174B, respectively. The projections of points 162, 168, and 172 on tomographic image planes $176_1$, $176_2$, and $176_N$ of the tomographic image detector, are referenced 178, 180, and 182, respectively. Right stereoscopic image plane 164A and coordinate system A, are associated with right view image 134R (FIG. 2). Left stereoscopic image plane 164B is associated with left view image 134L.

The origin of each of right stereoscopic image plane 164A and left stereoscopic image plane 164B, are separated by a distance D. In case stereoscopic image detector 112 employs a single image detector (not shown) to detect right view image 134R and left view image 134L, the distance D is equal to the interpupilar distance. In case stereoscopic image detector 112 employs two image detectors (not shown) to detect right view image 134R and left view image 134L, the distance D is equal to the distance between the optical centers of the two image detectors. Tomographic image detector 102 can be an infrared image detector. Stereoscopic image detector 112 acquires stereoscopic image pair 140 (i.e., right view image 134R and left view image 134L), on right stereoscopic image plane 164A and on left stereoscopic image plane 164B, respectively.

The coordinates of each of points 162, 168, and 172 in coordinate system A is referenced $(X_A, Y_A, Z_A)$. The coordinates of each of points 162, 168, and 172 in coordinate system B is referenced $(X_B, Y_B, Z_B)$. The coordinates of each of points 162, 168, and 172 projected on right stereoscopic image plane 164A is referenced $(X_{aR}, Y_{aR})$. The coordinates of each of points 162, 168, and 172, projected on left stereoscopic image plane 164B is referenced $(X_{aL}, Y_{aL})$.

The following holds for a point on object 160 and its projection on either of right stereoscopic image plane 164A or left stereoscopic image plane 164B, $$X_A = \frac{Z_A}{f_a} x_a \tag{1}$$

and, $$Y_A = \frac{Z_A}{f_a} y_a \tag{2}$$

where $f_a$ is a focal length associated with stereoscopic image detector 112, and $$x_a = \frac{x_{aL} + x_{aR}}{2}$$

and $y_a = y_{aL} = y_{aR}$ relate for example to right and left view images 134R and 134L.

The transformation matrix between coordinate systems A and B can be represented by, $$B = R \cdot A + T \tag{3}$$

where, $$B = [X_B \ Y_B \ Z_B]^T \tag{4}$$

$$R = \begin{bmatrix} r_{11} & r_{12} & r_{13} \\ r_{21} & r_{22} & r_{23} \\ r_{31} & r_{32} & r_{33} \end{bmatrix} \tag{5}$$

$$A = [X_A \ Y_A \ Z_A]^T \tag{6}$$

and, $$T = [t_x \ t_y \ t_z]^T \tag{7}$$

where R designates the rotation between the coordinate systems A and B, and T the translation between these coordinate systems. The right side of (5) includes nine elements, which are dependent rotation parameters, and which are trigonometric functions of three independent angles. Hence, the right side of (5) includes three unknown rotation parameters. Stereoscopic image pair 140 is regarded as a 3D reconstructed image, where the coordinates of a voxel (i.e., a three-dimensional picture element) in this image are referenced ($X_A$, $Y_A$, $Z_A$).

Tomographic image processor 110 (FIG. 2) can produce a 3D reconstructed image (i.e., tomographic image representation 138), by reconstructing a plurality of 2D images, such as 2D images 130A, 130B, and 130C, by employing a technique known in the art. In this case, tomographic image detector 102 can be for example, a CT, MRI, PET, SPECT, as well as an ultrasound image detector or an infrared image detector.

Image fusion processor 106 determines the rotation matrix R of (5), by determining the Quaternion vector $q_B^A$ between stereoscopic image pair 140 and tomographic image representation 138, where stereoscopic image pair 140 is associated with 3D coordinate system A (FIG. 4), and tomographic image representation 138 is associated with 3D coordinate system B. Each of stereoscopic image pair 140 and tomographic image representation 138 is regarded as N points $r_A$ and $r_B$, respectively. Image fusion processor 106 determines the centroid $\overline{r_A}$ for points $r_A$, and the centroid $\overline{r_B}$ for points $r_B$. Image fusion processor 106 can further perform a resealing operation on points $r_A$ and on points $r_B$, such that the value of the variance of each of the N points $r_A$ and $r_B$, relative to centroid $\overline{r_A}$ and centroid $\overline{r_B}$, respectively, is substantially equal to one.

The relation between coordinate systems A and B is, $$A = RB + T \tag{8}$$

where, $$A = [X_A Y_A Z_A]^T \tag{9}$$

and, $$B = [X_B Y_B Z_B]^T \tag{10}$$

The centroids of coordinate systems A and B are related by, $$A_{CENTEROID} = RB_{CENTEROID} + T \tag{11}$$

The difference of (8) and (11) yields, $$A - A_{CENTEROID} = R(B - B_{CENTEROID}) \tag{12}$$

Applying resealing to (12), yields the normalized relation between coordinate systems A and B, $$T_A(A - A_{CENTEROID}) = R_N T_B(B - B_{CENTEROID}) \tag{13}$$

where, $$T_A = \begin{bmatrix} \frac{1}{\sigma_x^A} & 0 & 0 \\ 0 & \frac{1}{\sigma_y^A} & 0 \\ 0 & 0 & \frac{1}{\sigma_z^A} \end{bmatrix} \tag{14}$$

$$T_B = \begin{bmatrix} \frac{1}{\sigma_x^B} & 0 & 0 \\ 0 & \frac{1}{\sigma_y^B} & 0 \\ 0 & 0 & \frac{1}{\sigma_z^B} \end{bmatrix} \tag{15}$$

and, $$R_N = T_B R T_B^{-1} \tag{16}$$

where $\sigma_x$, $\sigma_y$, and $\sigma_z$ are the scaling values along the X, Y, and Z axes, respectively.

Image fusion processor 106 determines the sums of products, $$S_{kl} = \sum_{i=1}^{N} k_{A,i} l_{B,i} \tag{17}$$

where $k_{A,i}$ is the coordinates (x, y, z) of point $r_A$ relative to the centroid $\overline{r_A}$, and where $l_{B,i}$ is the coordinates (x, y, z) of point $r_B$ relative to the centroid $\overline{r_B}$. It is noted that (8) can be applied to the rescaled values of $r_A$ and $r_B$ relative to centroid $\overline{r_A}$ and centroid $\overline{r_B}$, respectively. Image fusion processor 106 determines the following matrix according to (17), $$N = \begin{bmatrix} S_{xx}+S_{yy}+S_{zz} & S_{yz}-S_{zy} & S_{zx}-S_{xz} & S_{xy}-S_{yx} \\ S_{yz}-S_{zy} & S_{xx}-S_{yy}-S_{zz} & S_{xy}+S_{yx} & S_{zx}+S_{xz} \\ S_{zx}-S_{xz} & S_{xy}+S_{yx} & -S_{xx}+S_{yy}-S_{zz} & S_{yz}+S_{zy} \\ S_{xy}-S_{yx} & S_{zx}+S_{xz} & S_{yz}+S_{zy} & -S_{xx}-S_{yy}+S_{zz} \end{bmatrix} \quad (18)$$

determines the eigenvectors λ of (18), selects the largest eigenvector as the Quaternion vector $q_B{}^A$, and determines the rotation matrix $R_N$ between normalized coordinate systems A and B (Equation 13) according to, $$R_N = \begin{bmatrix} \lambda^2 + \rho_x^2 - \rho_y^2 - \rho_z^2 & 2(\rho_x\rho_y + \lambda\rho_z) & 2(\rho_x\rho_z + \lambda\rho_y) \\ 2(\rho_x\rho_y - \lambda\rho_z) & \lambda^2 - \rho_x^2 + \rho_y^2 - \rho_z^2 & 2(\rho_y\rho_z + \lambda\rho_x) \\ 2(\rho_x\rho_z + \lambda\rho_y) & 2(\rho_y\rho_z - \lambda\rho_x) & \lambda^2 - \rho_x^2 - \rho_y^2 + \rho_z^2 \end{bmatrix} \quad (19)$$

where λ is the real part of Quaternion vector $q_B{}^A$, and ρ is the imaginary part of Quaternion vector $q_B{}^A$. Image fusion processor 106 determines the rotation matrix R according to the Quaternion vector and (18) and (19) as, $$R = T_A^{-1} R_N T_B \quad (20)$$

Alternatively, image fusion processor 106 can determine $R_N$ by employing a linear least squares optimization technique with constraints, a non-linear least squares optimization technique, and the like.

Image fusion processor 106 determines the translation matrix T between coordinate systems A and B, according to the means (11) and (13) in coordinate systems A and B. Alternatively, image fusion processor 106 can determine the translation matrix T, according to (8) by employing a least squares optimization technique. Image fusion processor 106 determines the scaling according to (14) and (15). Each voxel in the 3D reconstructed image which tomographic image detector 102 produces, is associated with three coordinates (x, y, z) and with a light intensity value in gray scale (i.e., four parameters in total).

Following is a description of the procedure for superimposing a stereoscopic image representation, acquired by tomographic image detector 102, on stereoscopic image pair 140, acquired by stereoscopic image detector 112. Image fusion processor 106 produces a stereoscopic augmented image, by superimposing a right view 2D projection and a left view 2D projection, respective of tomographic image representation 138, on right view image 134R and left view image 134L, respectively. Thus, the user can gain a stereoscopic perception of the 3D reconstructed image detected by tomographic image detector 112, as well as stereoscopic image pair 140 detected by stereoscopic image detector 112.

Image fusion processor 106 determines the right view 2D projection and the left view 2D projection, by projecting the 3D reconstructed image respective of tomographic image detector 102, on a right image plane (not shown) and a left image plane (not shown), respective of stereoscopic image detector 112. The pair of the right view 2D projection and the left view 2D projection are herein below referred to as a computed stereoscopic image.

For this purpose, it is necessary for image fusion processor 106 to determine the coordinates of the right image plane and the left image plane, relative to those of the 3D reconstructed image. Image fusion processor 106 determines these coordinates, by determining a right transformation matrix and a left transformation matrix respective of tomographic image representation 138 and stereoscopic image pair 140 (i.e., registering images of two modalities). Each transformation matrix determines the respective image plane.

Image fusion processor 106 can register the two image modalities according to one of the methods described herein above. Image fusion processor 106 reconstructs a 3D image respective of stereoscopic image pair 140, and determines the three coordinates of at least three points in stereoscopic image pair 140, in order to register the images of the two modalities, and to determine the coordinates of the right image plane and the left image plane. Image fusion processor 106 can determine the Z coordinate of each of these three points (i.e., the coordinate along an optical axis respective of stereoscopic image detector 112), according to the disparity value of the respective point in stereoscopic image pair 140. Image fusion processor 106 can determine these disparities by employing a method known in the art. In case system 100 employs fiducials 118A, 118B, and 118C, image fusion processor 106 performs the registration procedure by determining the rotation and translation and the scaling of an image (not shown) of base 120 (FIG. 3A) acquired by stereoscopic image detector 112, relative to that of image 132B of a cross section of the fiducial acquired by tomographic image detector 102.

Image fusion processor 106 produces the right view 2D projection and the left view 2D projection, such that every pair of pixels corresponds to a respective voxel in the 3D reconstructed image of stereoscopic image pair 140. The value of the light intensity of this pair of pixels are substantially the same, and are furthermore determined according to the value of the light intensity of all the voxels in the 3D reconstructed image, whose (x, y) coordinates are the same, and correspond to this pair of pixels. Image fusion processor 106 can determine the value of the light intensity of this pair of pixels, by applying a predetermined function to the values of the light intensity (i.e., the z coordinates) of all the voxels corresponding to this pair of pixels, for example by determining the sum of these values of light intensity, and the like.

Generally, tomographic image processor 110 represents the light intensity of each voxel of the 3D reconstructed image, in the gray scale, and thus each of the right view 2D projection and the left view 2D projection is represented in gray scale. Image fusion processor 106 can further employ a look-up table to assign a certain color value to the light intensity of this pair of pixels, in a gray scale, thereby providing a color image.

Following is a description of registering a 3D tomographic image representation with a stereoscopic image pair, where the stereoscopic image pair is regarded as a 3D reconstructed image, and where the surface of the organ is substantially flat, or alternatively, where at least three points of the surface of the organ lie on a substantially flat anatomic plane.

The tomographic image detector acquires a first set of images of these points on a first flat plane, and the stereoscopic image detector acquires a second set of images of these points, on a second flat plane. The image fusion processor determines the line at which the first plane and the second plane intersect. The image fusion processor rotates the first plane and the second plane about this line, so that the first plane and the second plane are located on the same plane, and thereby determines an angle of rotation α, and a first Quaternion vector.

The image fusion processor rotates one of the first plane and the second plane about the normal common to both the first plane and the second plane, so that the points on the first plane and on the second plane are aligned, thereby determining an angle of rotation β, and a second Quaternion vector. The image fusion processor determines the rotation matrix between the stereoscopic image pair and the tomographic image representation, according to the first Quaternion vector and the second Quaternion vector. The image fusion processor determines the translation matrix between the stereoscopic image pair and the tomographic image representation for example, according to (11), as described herein above, and further determines the transformation matrix between the stereoscopic image pair and the tomographic image representation.

In the following description, each of stereoscopic image pair 140 and tomographic image representation 138, is regarded as a 3D reconstructed image. Therefore, stereoscopic image pair 140 can be represented by a plurality of points in a first 3D coordinate system, and tomographic image representation 138 can be represented by a plurality of points in a second 3D coordinate system. Image fusion processor 106 determines the transformation matrix between stereoscopic image pair 140 and tomographic image representation 138, by identifying the corresponding points in stereoscopic image pair 140 and in tomographic image representation 138. According to the disclosed technique, image fusion processor 106 can determine the corresponding points by following different procedures, as described herein below.

According to an aspect of the disclosed technique, image fusion processor 106 determines the corresponding points in stereoscopic image pair 140 and in tomographic image representation 138, according to an iterative closest points (ICP) procedure. In a first mode of operation, image fusion processor 106 determines an initial hypothesis, that a number of these 3D points in stereoscopic image pair 140 and in tomographic image representation 138, correspond to one another (i.e., 3D corresponding points), and thereby determines the transformation matrix between stereoscopic image pair 140 and tomographic image representation 138.

According to one aspect of the disclosed technique, image fusion processor 106 applies the transformation matrix to the 3D corresponding points in stereoscopic image pair 140 and tomographic image representation 138, and identifies the 3D points in stereoscopic image pair 140 and in tomographic image representation 138 which do not correspond to one another (i.e., 3D non-corresponding points). Image fusion processor 106 discards the 3D non-corresponding points and repeats the first mode and the second mode of operation, until the procedure converges.

According to another aspect of the disclosed technique, image fusion processor 106 determines the corresponding points according to a distance invariant method, as follows. Image fusion processor 106 selects a first set of three points for example, in stereoscopic image pair 140, and determines the values of a set of three mutual distances between the three points in the first set of three points. Image fusion processor 106 can determine the set of three mutual distances, for example, according to the gradient or the curvature of each point. Image fusion processor 106 determines a second set of three points in tomographic image representation 138, which are associated with substantially the same values of the set of three mutual distances.

Image fusion processor 106 determines a fourth point in each of stereoscopic image pair 140 and tomographic image representation 138, whose distance from the three points, in the first set of three points and in the second set of three points, respectively, is substantially the same. Image fusion processor 106 performs the above procedure with respect to additional points in stereoscopic image pair 140 and in tomographic image representation 138, until image fusion processor 106 determines substantially all the corresponding points.

According to a further aspect of the disclosed technique, image fusion processor 106 determines the corresponding points according to a feature based method, as follows. Image fusion processor 106 forms a first set of spheres having a selected radius, about each of the points for example, in stereoscopic image pair 140, and determines the number of other points (i.e., a first set of neighbors) which are located within each sphere in the first set of spheres. Image fusion processor 106 forms a second set of spheres whose radii are substantially equal to the selected radius, around each of the points in tomographic image representation 138, and determines the number of neighbors to the central point in each sphere in the second set of spheres. Image fusion processor 106 determines substantially every pair of corresponding points which are associated with the same number of neighbors.

According to another aspect of the disclosed technique, image fusion processor 106 determines the corresponding points according to a 3D cross correlation method, as follows. Image fusion processor 106 forms a volume about a point for example, in stereoscopic image pair 140, and determines the corresponding point in tomographic image representation 138, by forming similar volumes about selected points in tomographic image representation 138, and by comparing the characteristics (e.g., intensity) of the volume in stereoscopic image pair 140, with the characteristics of the selected volumes in tomographic image representation 138.

Figure 5:
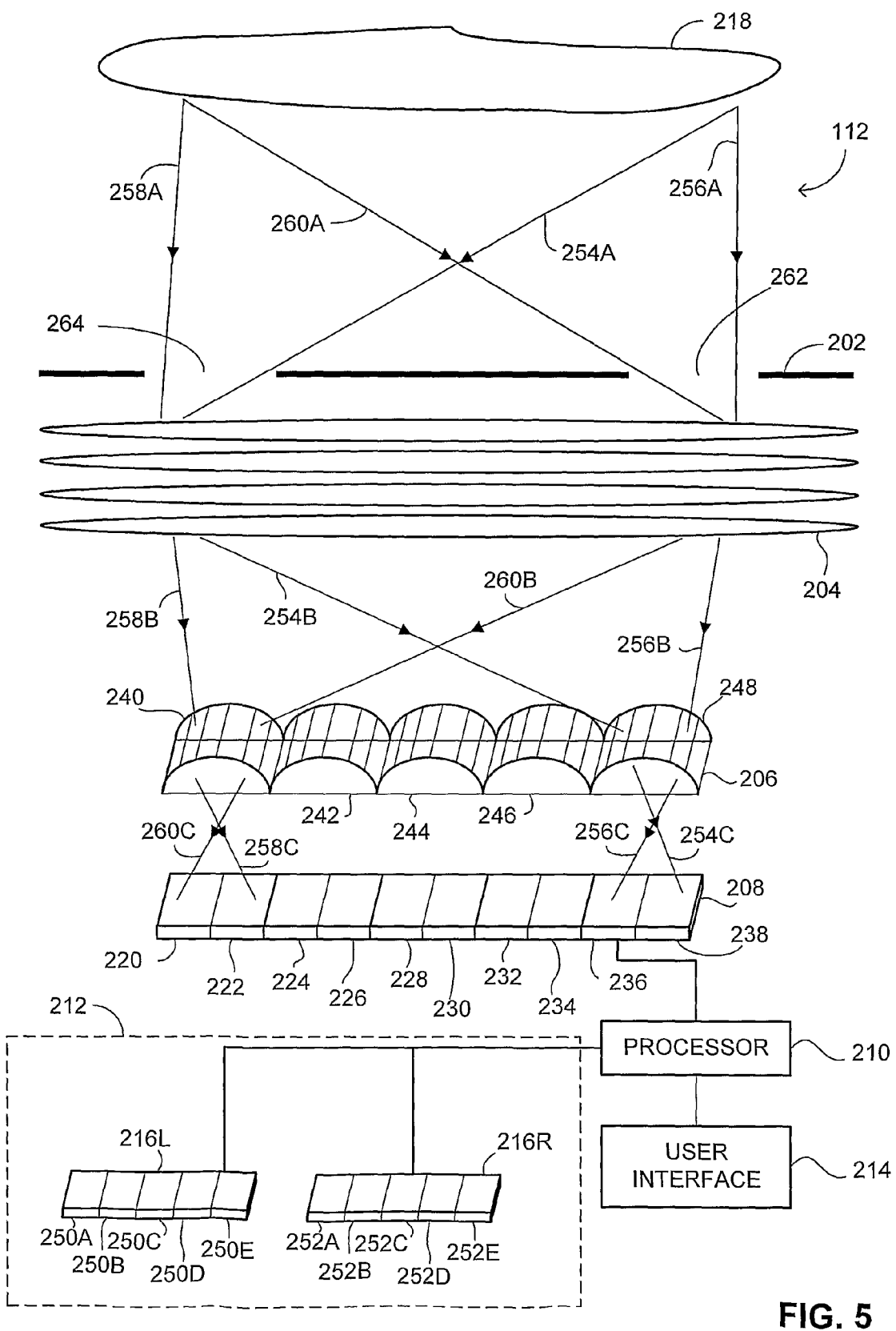
FIG. 5 is a schematic illustration of the stereoscopic image detector of the system of FIG. 2.

Reference is now made to FIG. 5, which is a schematic illustration of the stereoscopic image detector of the system of FIG. 2, generally referenced 112. Stereoscopic image detector 112 includes a dual aperture element 202, an objective lens array 204, a lenticular lens layer 206, an image detector 208, a processor 210, a display 212, and a user interface 214. Display 212 includes two display units 216L and 216R. Image detector 208 is coupled with processor 210. Processor 210 is further coupled with display 212 and with user interface 214. Stereoscopic image detector 112 acquires an image of an object 218. Objective lens array 204 includes a plurality of optical elements, and produces at least one intermediate image of an object detected thereby.

Image detector 208 includes a plurality of sensors 220, 222, 224, 226, 228, 230, 232, 234, 236, and 238. Lenticular lens layer 206 includes a plurality of lenticular lens elements 240, 242, 244, 246, and 248. Each one of the lenticular lens elements is located above two light sensors, in a way that lenticular lens element 240 is located above sensors 220 and 222, lenticular lens element 242 is located above sensors 224 and 226, lenticular lens element 244 is located above sensors 228 and 230, lenticular lens element 246 is located above sensors 232 and 234, and lenticular lens element 248 is located above sensors 236 and 238.

Light sensors 220, 222, 224, 226, 228, 230, 232, 234, 236, and 238 detect light as directed by the lenticular lens elements 240, 242, 244, 246, and 248, and provide respective information to processor 210. Processor 210 processes this information, produces a pair of images, as will be explained in detail herein below, and provides them to display units 216R and 216L, which in turn produce visual representations of these images.

In general, each lenticular lens element directs light rays, which arrive from a predetermined direction, to a predetermined location and light rays which arrive from another predetermined direction, to another predetermined location. Hence, stereoscopic image detector 112 utilizes lenticular lens layer 206 to distinguish between a right view image and a left view image, as described herein below.

Each of the display units 216R and 216L includes a plurality of display units also known as pixels. Display unit 216L includes pixels 250A, 250B, 250C, 250D, and 250E. Display unit 216R includes pixels 252A, 252B, 252C, 252D, and 252E. Using these pixels, each of the display units produces an image, according to data provided from processor 210. A user (not shown) views each of the two images with a different eye, thereby gaining a stereoscopic perception.

Light rays 254A, and 256A represent a right-side image of object 218. Light rays 258A, and 260A represent a left-side image of object 218. Light rays 260A and 256A pass through an aperture 262 of dual aperture element 202, and light rays 258A and 254A pass through an aperture 264 of dual aperture element 202, toward objective lens array 204. Objective lens array 204 directs light rays 258A, 260A, 254A, and 256A, so as to focus them on a plane (not shown) determined by image detector 208, as light rays 258B, 260B, 254B, and 256B, respectively. Hence, light rays 260B and 256B represent a focused right-side view of object 218, and light rays 258B and 254B represent a focused left-side view of object 218.

Lenticular lens layer 206 directs focused right-side view light rays 260B and 256B to light sensors 220 and 236, respectively, as light rays 260C and 256C. In addition, lenticular lens layer 206 directs focused left-side view light rays 258B and 254B to light sensors 222 and 238, respectively, as light rays 258C, and 254C. In general, light sensors 222, 226, 230, 234, and 238 detect light rays which relate to a left-side view image of object 218, and light sensors 220, 224, 228, 232, and 236, detect light rays which relate to a right-side view image of object 218.

Hence, light sensors 220, 224, 228, 232, and 236 detect the left-side image of image 218, while light sensors 222, 226, 230, 234, and 238 acquires the right-side view image of object 218. Image detector 208 provides data relating to the detected light intensity at each of the light sensors to processor 210.

Processor 210 processes this data, produces a right-side image from the data relating to the right-side image, and a left-side image from the data relating to the left side, and provides the respective image to respective display unit 216R and 216L.

In the present example, processor 210 utilizes the data received from sensors 220, 224, 228, 232, and 236 to determine the data provided to pixels 252A, 252B, 252C, 252D and 252E. Similarly, processor 210 utilizes the data received from sensors 222, 226, 230, 234, and 238 to determine the data which is to be provided to pixels 250A, 250B, 250C, 250D, and 250E. According to the disclosed technique, the right-side image and the left-side image are detected at the same time and hence, can also be displayed at the same time.

It will be appreciated by persons skilled in the art that the disclosed technique is not limited to what has been particularly shown and described hereinabove. Rather the scope of the disclosed technique is defined only by the claims, which follow.

The invention claimed is:

1. System for displaying an augmented image of an organ of a patient, the system comprising: an image fusion processor coupled with a stereoscopic image detector, a tomographic image processor, and with a display, said tomographic image processor being further coupled with a tomographic image detector, said stereoscopic image detector producing a pair of stereoscopic images respective of an exposed region of said organ, said tomographic image detector acquiring at least one two-dimensional image of a concealed region of said organ, said concealed region being concealed from the view of said stereoscopic image detector, said tomographic image processor producing at least one tomographic image representation of said concealed region, according to an output of said tomographic image detector, said image fusion processor registering said pair of stereoscopic images with said at least one tomographic image representation, said image fusion processor producing said augmented image, by superimposing said at least one tomographic image representation on said pair of stereoscopic images, said display displaying said augmented image.

2. The system according to claim 1, further comprising a user interface coupled with said image fusion processor, said image fusion processor controlling at least one visual feature of at least one of said 5 at least one tomographic image representation and said pair of stereoscopic images, according to an output of said user interface.

3. The system according to claim 1, wherein the type of said tomographic image detector is selected from the list consisting of: o ultrasonic; infrared; computer tomography; magnetic resonance imager; positron emission tomography; and single photon emission computer tomography.

4. The system according to claim 1, wherein said display is selected from the list consisting of: cathode ray tube; autostereoscopic display; head-mounted display; volumetric display; and multi liquid crystal display.

5. The system according to claim 1, wherein said at least one tomographic image representation is a three-dimensional image reconstructed by said image fusion processor, according to said at least one two-dimensional image.

6. The system according to claim 1, wherein said at least one 0 tomographic image representation includes said at least one two-dimensional image.

7. The system according to claim 1, wherein said image fusion processor registers said pair of stereoscopic images with said at least 5 one tomographic image representation, according to a first set of three-dimensional coordinates respective of a first set of at least three points in a first reconstructed three-dimensional image, reconstructed from said pair of stereoscopic images, and according to a second set of three-dimensional coordinates respective of a second set of at o least three points, in said at least one tomographic image representation.

8. The system according to claim 7, wherein each of said first set of at least three points and said second set of at least three points, is associated with an anatomic landmark located on said exposed region, wherein said stereoscopic image detector acquires a first image of said anatomic landmark, said first image including said first set of at least three points, and wherein said tomographic image detector acquires a second image of said anatomic landmark, said second image including said second set of at least three points.

9. The system according to claim 7, wherein each of said first set of at least three points and said second set of at least three points, is associated with at least one fiducial which is attached to said organ, wherein said stereoscopic image detector acquires a first image of said at least one fiducial, in said exposed region, said first image including said first set of at least three points, and wherein said tomographic image detector acquires a second image of said at least one fiducial, in said concealed region, said second image including said second set of at least three points.

10. The system according to claim 9, wherein said at least one fiducial includes a single fiducial, in the form of a conical pyramid, wherein said first image is associated with a base of said single fiducial, and wherein said second image is associated with a cross section of said single fiducial.

11. The system according to claim 10, wherein the geometry of said base is a polygon selected from the list consisting of: square; rectangle; triangle; pentagon; hexagon; parallelogram; and trapezoid.

12. The system according to claim 9, wherein said at least one fiducial is o constructed from a plurality of layers, each of said layers having a different physical characteristic, such that said tomographic image processor can determine the location of a respective one of said at least one two-dimensional image, along a longitudinal axis of a respective one of said at least one fiducial, relative to a base of said 5 respective at least one fiducial, according to said different physical characteristic.

13. The system according to claim 7, wherein said image fusion processor determines a first coordinate and a second coordinate of o said first set of three-dimensional coordinates, according to indices of respective pixels respective of said first set of at least three points, in a first image detected by said stereoscopic image detector, wherein said image fusion processor determines a third coordinate of said first set of three-dimensional coordinates, in a 5 direction along an optical axis respective of said stereoscopic image detector, according to a disparity value respective of respective points of said first set of at least three points, and wherein said image fusion processor determines said second set of three-dimensional coordinates, according an output of said 0 tomographic image processor.

14. The system according to claim 9, wherein said at least one fiducial includes a single fiducial in the form of a conic pyramid.

15. The system according to claim 9, wherein said at least one fiducial includes at least three fiducials, each of said at least one fiducials being in the form of a right circular cylinder.

16. Method for displaying an augmented image of an organ of a patient, the method comprising the procedures of: registering a pair of stereoscopic images of an exposed region of said organ, with at least one tomographic image representation respective of a concealed region of said organ, said concealed region being concealed from the view of a stereoscopic image detector, acquiring said pair of stereoscopic images; producing said augmented image, by superimposing said at least one tomographic image representation on said pair of stereoscopic images; and displaying said augmented image.

17. The method according to claim 16, comprising a preliminary procedure of acquiring said pair of stereoscopic images by said stereoscopic image detector.

18. The method according to claim 16, comprising a preliminary 5 procedure of producing said at least one tomographic image representation by a tomographic image processor, according to at least one two-dimensional image of said concealed region, detected by a tomographic image detector.

19. The method according to claim 16, comprising a procedure of controlling at least one visual feature respective of at least one of said at least one tomographic image representation and said pair of stereoscopic images, before performing said procedure of displaying.

20. The method according to claim 16, comprising a preliminary procedure of producing an image of a selected portion of said concealed region, by applying a segmentation algorithm to said tomographic image representation.

21. The method according to claim 16, comprising a preliminary procedure of reconstructing a three-dimensional image, according to at least one two-dimensional image of said concealed region, thereby producing said at least one tomographic image representation.

22. The method according to claim 16, wherein said at least one tomographic image representation is a three-dimensional image reconstructed by said image fusion processor, according to said at least one two-dimensional image.

23. The method according to claim 16, wherein said at least one tomographic image representation includes at least one two-dimensional image of said concealed region.

24. The method according to claim 16, wherein said procedure of producing comprises the procedures of: producing a first two-dimensional projection, by projecting a three-dimensional image of said organ, on a first image plane defined by a stereoscopic image detector acquiring said pair of stereoscopic images, according to at least one two-dimensional image of said concealed region, said first image plane being determined according to said procedure of registering; and producing a second two-dimensional projection, by projecting said three-dimensional image on a second image plane defined by said stereoscopic image detector, according to said at least one two-dimensional image, said second image plane being determined according to said procedure of registering.

25. The method according to claim 24, wherein each of said procedures of producing said first two-dimensional projection and said second two-dimensional projection, is performed by defining a first set of pixels in said at least one tomographic image representation, and defining a second set of pixels in said pair of stereoscopic images, and wherein every pixel in said first set of pixels substantially corresponds to a matching pixel in said second set of pixels.

26. The method according to claim 16, wherein said procedure of registering is enhanced according to an output of a position and orientation determining system, coupled with said stereoscopic image detector and with a tomographic image detector, acquiring at least one two-dimensional image of said concealed region.

27. The method according to claim 26, wherein the type of said position and orientation determining system is selected from the list consisting of: electromagnetic; optic; and sonic.

28. The method according to claim 16, wherein said procedure of registering is performed according to a first set of three-dimensional coordinates respective of a first set of at least three points in a first reconstructed three-dimensional image, reconstructed from said pair of stereoscopic images, and according to a second set of three-dimensional coordinates respective of a second set of at least three points, in said at least one tomographic image representation.

29. The method according to claim 28, wherein each of said first set of at least three points and said second set of at least three points, is associated with an anatomic landmark located on said exposed region, wherein said stereoscopic image detector acquires a first image of said anatomic landmark, said first image including said first set of at least three points, and wherein a tomographic image detector, acquiring at least one two-dimensional image of said concealed region, acquires a second image of said anatomic landmark, said second image including said second set of at least three points.

30. The method according to claim 28, wherein each of said first set of at least three points and said second set of at least three points, is associated with at least one fiducial which is attached to said organ, wherein said stereoscopic image detector acquires a first image of said at least one fiducial, in said exposed region, said first image including said first set of at least three points, and wherein said tomographic image detector, acquiring at least one two-dimensional image of said concealed region, acquires a second image of said at least one fiducial, in said concealed region, said second image including said second set of at least three points.

31. The method according to claim 30, wherein said at least one fiducial is constructed from a plurality of layers, each of said layers having a different physical characteristic, such that a tomographic image processor producing said tomographic image representation, can determine the location of a respective one of said at least one two-dimensional image, along a longitudinal axis of a respective one of said at least one fiducial, relative to a base of said respective at least one fiducial, according to said different physical characteristic.

32. The method according to claim 28, further comprising the procedures of: determining a first coordinate and a second coordinate of said first set of three-dimensional coordinates, according to indices of respective pixels respective of said first set of at least three points, in a first image detected by said stereoscopic image detector; determining a third coordinate of said first set of three-dimensional coordinates, in a direction along an optical axis respective of said stereoscopic image detector, according to a disparity value respective of respective points of said first set of at least three points, and determining said second set of three-dimensional coordinates, according an output of a tomographic image processor producing said tomographic image representation.

33. The method according to claim 16, further comprising a procedure of applying an attenuation function to said at least one tomographic image representation, before performing said procedure of displaying, such that a most recent light intensity of the most recent one of said at least one tomographic image representation, is greater than a least recent light intensity of the least recent one of said at least one tomographic image representation.

34. The method according to claim 16, wherein said procedure of registering is performed by: determining a rotation of said at least one tomographic image representation relative to said pair of stereoscopic images, according to a Quaternion vector respective of said at least one tomographic image representation and said pair of stereoscopic images; determining a translation of said at least one tomographic image representation relative to said pair of stereoscopic images, according to a first centroid respective of a first coordinate system respective of said at least one tomographic image representation, and a second centroid respective of a second coordinate system respective of said pair of stereoscopic image, and determining a scale of at least one of said at least one tomographic image representation relative to said pair of stereoscopic images, according to a first set of scaling values respective of said first coordinate system, and a second set of scaling values respective of said second coordinate system.

35. The method according to claim 16, wherein said registering procedure is performed by determining a rotation between said at least one tomographic image representation and said pair of stereoscopic images, by determining a first Quaternion vector and a second Quaternion vector, said first Quaternion vector being determined by: acquiring a first image of a set of at least three points, located on a flat anatomic plane associated with said organ; acquiring a second image of said set of at least three points, by said stereoscopic image detector; determining a line at which a first plane respective of said first image, intersects a second plane respective of said second image, and rotating at least one of said first plane and said second plane, about said line, such that said first plane and said second plane are located substantially on the same plane; and said second Quaternion vector being determined by rotating at least one of said first plane and said second plane, about a normal common to said first plane and said second plane, such that said set of at least three points in said first image are substantially aligned with those on said second image.

36. The method according to claim 16, wherein said procedure of registering is performed by determining a plurality of corresponding points in said at least one tomographic image representation and in said pair of stereoscopic images.

37. The method according to claim 36, wherein said corresponding points are determined according to a procedure selected from the list consisting of: iterative closest points; distance invariant; feature based; and three-dimensional cross correlation.

* * * * *

UNITED STATES PATENT AND TRADEMARK OFFICE
CERTIFICATE OF CORRECTION

PATENT NO.       : 7,480,402 B2
APPLICATION NO.  : 11/912099
DATED            : January 20, 2009
INVENTOR(S)      : Bar-Zohar et al.

It is certified that error appears in the above-identified patent and that said Letters Patent is hereby corrected as shown below:

Col. 16, line 26, claim 2: "said 5 at least" should read --said at least--

Col. 16, line 31, claim 3: "of: o ultrasonic;" should read --of: ultrasonic;--

Col. 16, line 43, claim 6: "one 0 tomographic" should read --one tomographic--

Col. 16, line 47, claim 7: "least 5 one tomographic" should read --least one tomographic--

Col. 16, line 53, claim 7: "o least three points," should read --least three points,--

Col. 17, line 17, claim 12: "is o constructed from" should read --is constructed from--

Col. 17, line 22, claim 12: "of said 5 respective" should read --of said respective--

Col. 17, line 27, claim 13: "of o said first" should read --of said first--

Col. 17, line 32, claim 13: "in a 5 direction along" should read --in a direction along--

Col. 17, line 37, claim 13: "of said 0 tomographic" should read --of said tomographic--

Col. 17, lines 60-61, claim 18: "preliminary 5 procedure of" should read --preliminary procedure of--

Signed and Sealed this

Ninth Day of November, 2010

David J. Kappos
*Director of the United States Patent and Trademark Office*